(12) United States Patent
Yanagisawa et al.

(10) Patent No.: US 7,053,389 B2
(45) Date of Patent: May 30, 2006

(54) CHARGED PARTICLE THERAPY SYSTEM, RANGE MODULATION WHEEL DEVICE, AND METHOD OF INSTALLING RANGE MODULATION WHEEL DEVICE

(75) Inventors: Masaki Yanagisawa, Hitachi (JP); Hiroshi Akiyama, Hitachiohta (JP); Koji Matsuda, Hitachi (JP); Hisataka Fujimaki, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 84 days.

(21) Appl. No.: 10/917,458

(22) Filed: Aug. 13, 2004

(65) Prior Publication Data
US 2005/0051740 A1 Mar. 10, 2005

(30) Foreign Application Priority Data
Sep. 10, 2003 (JP) .............................. 2003-317656

(51) Int. Cl.
*G21G 5/00* (2006.01)
(52) U.S. Cl. ................. 250/492.3; 250/492.1; 250/492.2; 250/396 R; 250/505.1; 315/502; 315/507; 315/111.61; 378/65
(58) Field of Classification Search ..................... None
See application file for complete search history.

(56) References Cited

U.S. PATENT DOCUMENTS 6,717,162 B1 * 4/2004 Jongen ..................... 250/505.1

OTHER PUBLICATIONS

"Review of Scientific Instruments", vol. 64, No. 8, pp. 2074-2086 (Aug. 1993).

* cited by examiner

*Primary Examiner*—Nikita Wells
*Assistant Examiner*—Zia R. Hashmi
(74) *Attorney, Agent, or Firm*—Dickstein Shapiro Morin & Oshinsky LLP

(57) ABSTRACT

The invention provides a charged particle therapy system capable of increasing the number of patients treated. An irradiation filed forming apparatus for irradiating a charged particle beam extracted from a charged particle beam generator to an irradiation target includes an RMW device. The RMW device comprises a housing and an RMW disposed within the housing. A rotary shaft of the RMW is rotatably mounted to the housing. The RMW device is detachably installed in an RMW holding member provided in a casing of the irradiation filed forming apparatus. The housing can be placed in contact with the RMW holding member, and hence positioning of the rotary shaft of the RMW to a predetermined position can be performed in a short time. This contributes to cutting a time required for treatment per patient and increasing the number of patients treated.

14 Claims, 7 Drawing Sheets

CHARGED PARTICLE THERAPY SYSTEM, RANGE MODULATION WHEEL DEVICE, AND METHOD OF INSTALLING RANGE MODULATION WHEEL DEVICE

BACKGROUND OF THE INVENTION

1. Field of the Invention

The present invention relates to a charged particle therapy system, and more particularly to a charged particle therapy system having a range modulation wheel (hereinafter abbreviated to "RMW"), in which a charged particle beam, such as a proton or carbon ion beam, is irradiated to a tumor for treatment.

2. Description of the Related Art

A known charged particle therapy system comprises a charged particle beam generator, an ion beam transport system, and a rotating irradiation apparatus. The charged particle beam generator includes a synchrotron (or a cyclotron) as an accelerator. A charged particle beam accelerated to setting energy by the synchrotron reaches the rotating irradiation apparatus through the ion beam transport system (first ion beam transport system). The rotating irradiation apparatus comprises an irradiation-apparatus ion beam transport system (second ion beam transport system), an irradiation field forming apparatus, and a rotating apparatus (rotating gantry) for rotating the second ion beam transport system and the irradiation field forming apparatus as an integral structure. The ion beam is irradiated to a tumor, e.g., a cancer, in the body of a patient from the irradiation field forming apparatus through the second ion beam transport system.

The irradiation field forming apparatus has the functions of not only shaping the ion beam extracted from the charged particle beam generator in match with a three-dimensional shape of the tumor as an irradiation target, thereby to form an irradiation field, but also adjusting the dose in the irradiation field. As one of methods for irradiating the ion beam in the desired dose in match with the shape of the irradiation target, a double scattering method is known which makes uniform the dose of the ion beam with two types of scatterers arranged at a distance between them in the axial direction of the ion beam by utilizing the fact that the dose of an ion beam having passed a scatterer has a nearly Gaussian distribution (see, e.g., FIG. 36 in page 2081 of Non-Patent Reference 1; "REVIEW OF SCIENTIFIC INSTRUMENTS", VOLUME 64, NUMBER 8 (AUGUST 1993), P2074–2086). As another irradiation method, there is also known a wobbler method for making uniform the dose of the ion beam by using two scanning magnets (see, e.g., FIG. 41 in page 2084 of Non-Patent Reference 1).

In those irradiation methods, a Bragg peak spreading-out (SOBP) device is employed to make uniform the dose of the ion beam in the depth direction of the tumor in the patient body (i.e., in the direction of irradiation of the ion beam). Examples of the SOBP device include a ridge filter (see, e.g., FIG. 31 in page 2078 and FIG. 41 in page 2084 of Non-Patent Reference 1) and an RWM (see, e.g., FIG. 30 in page 2077 of Non-Patent Reference 1).

The RWM is rotatably installed on a path of the ion beam within the irradiation field forming apparatus. The RWM has a plurality of blades extending radially from a rotary shaft, and distal ends of the blades are joined to a cylindrical member. The cylindrical member is concentric to the rotary shaft. Each blade has multiple steps each having a different thickness and arranged successively in the circumferential direction of the RWM. Each step having a different thickness is extended from the rotary shaft to the cylindrical member. The ion beam propagating in the irradiation field forming apparatus passes those steps when passing through the rotating RMW. Therefore, the ion beam having passed the RWM has a plurality of energy components corresponding to the thickness of each of the steps through which the ion beam has passed. As a result, the dose of the ion beam is made uniform in the depth direction of the tumor in the patient body.

SUMMARY OF THE INVENTION

The RMW is installed in the irradiation field forming apparatus corresponding to each patient. At that time, the rotary shaft of the RMW must be aligned with a rotary shaft of an RMW driver mounted in the irradiation field forming apparatus. The operation for aligning the rotary shaft of the RMW and the rotary shaft of the RMW driver with each other is performed by a radiation engineer. However, such an alignment operation is very difficult to carry out and installation of the RMW to the irradiation field forming apparatus takes a lot of time.

ACCORDINGLY, IT IS AN OBJECT OF THE PRESENT INVENTION TO PROVIDE A CHARGED PARTICLE THERAPY SYSTEM, A RANGE MODULATION WHEEL DEVICE, AND A METHOD OF INSTALLING THE RANGE MODULATION WHEEL DEVICE, WHICH CAN INCREASE THE NUMBER OF PATIENTS TREATED.

To achieve the above object, according to a first aspect of the present invention, there is provided a charged particle therapy system in which a range modulation wheel device provided in charged particle beam irradiation apparatus comprises a housing and a range modulation wheel disposed in the housing and rotatably mounted thereto so as to allow a charged particle beam to pass through the range modulation wheel.

With the first aspect of the present invention, the range modulation wheel device has the housing, and the housing can be placed in contact with a component of the charged particle beam irradiation apparatus. Therefore, positioning of the rotary shaft of the range modulation wheel to a predetermined position can be performed in a short time. This contributes to cutting a time required for treatment per patient and increasing the number of patients treated.

To achieve the above object, a second aspect of the present invention, there is provided a range modulation wheel device comprising a housing and a range modulation wheel disposed in the housing and rotatably mounted thereto so as to allow a charged particle beam to pass through the range modulation wheel.

Because the range modulation wheel device has the housing, the second aspect of the present invention can also provide the same advantages as those obtained with the first aspect of the present invention.

To achieve the above object, a third aspect of the present invention, there is provided a method of installing a range modulation wheel device, the method comprising the steps of preparing a range modulation wheel device comprising a housing and a range modulation wheel disposed in said housing and rotatably mounted thereto, inserting said range modulation wheel device into a holding member provided in a charged particle beam irradiation apparatus, and pushing said housing against said holding member by a pushing member.

Because the range modulation wheel device has the housing, the third aspect of the present invention can also provide the same advantages as those obtained with the first aspect of the present invention.

According to the present invention, it is possible to cut a time required for treatment and to increase the number of patients treated.

BRIEF DESCRIPTION OF THE DRAWINGS

FIGS. 9A and 9B are side views of an RMW device according to a second embodiment; namely.

DESCRIPTION OF THE PREFERRED EMBODIMENTS

Embodiments of the present invention will be described in detail below with reference to the drawings.

[First Embodiment]

Figure 2:
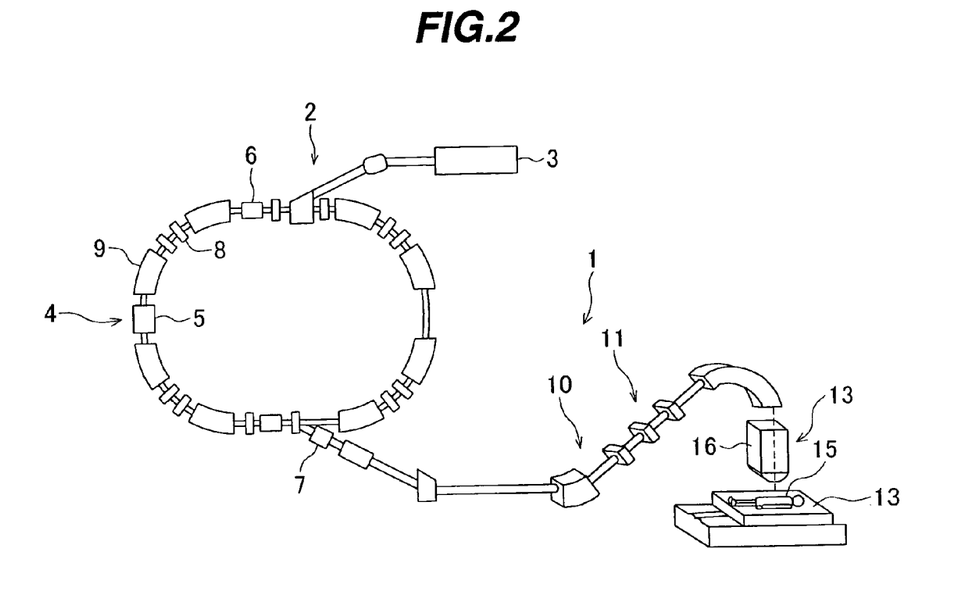
FIG. 2 is an illustration schematically showing an overall construction of the charged particle therapy system according to the first embodiment of the present invention.

A charged particle therapy system representing a first preferred embodiment of the present invention will be described with reference to FIG. 2. A charged particle therapy system 1 of this embodiment comprises a charged particle beam generator 2 and an irradiation field forming apparatus (charged particle beam irradiation apparatus) 13. The charged particle beam generator 2 comprises an ion source (not shown), a pre-accelerator 3, and a synchrotron 4. Ions (e.g., protons (or carbon ions)) generated by the ion source are accelerated by the pre-accelerator (e.g., a linear accelerator) 3. An ion beam (charged particle beam) emitted from the pre-accelerator 3 enters the synchrotron 4. The ion beam is accelerated in the synchrotron 4 in which it is given with energy by radio-frequency (RF) power applied from an RF-accelerating cavity 5. After energy of the ion beam circulating in the synchrotron 4 has been increased up to a setting level, an RF wave is applied to the circulating ion beam from an RF-applying device 6 for beam extraction. With the application of the RF wave, the ion beam circulating within a separatrix is forced to transit to the outside of the separatrix and to exit from the synchrotron 4 through a beam extraction deflector 7. At the time of extracting the ion beam, currents supplied to magnets, such as quadrupole magnets 8 and bending magnets 9, disposed in the synchrotron 4 are held at setting current values, and therefore the separatrix is also held substantially constant. The extraction of the ion beam from the synchrotron 4 is stopped by ceasing the application of the RF power to the RF-applying device 6.

The ion beam extracted from the synchrotron 4 is transported to the irradiation field forming apparatus 13, serving as the irradiation apparatus, through an ion beam transport system 10. An inverted U-shaped section 11 as a part of the ion beam transport system 10 and the irradiation field forming apparatus 13 are mounted on a rotating gantry (not shown) that is rotatable as an integral structure. The ion beam is irradiated from the irradiation field forming apparatus 13 to a tumor K in the body of a patient 15 lying on a treatment bench (couch) 14.

Figure 1:
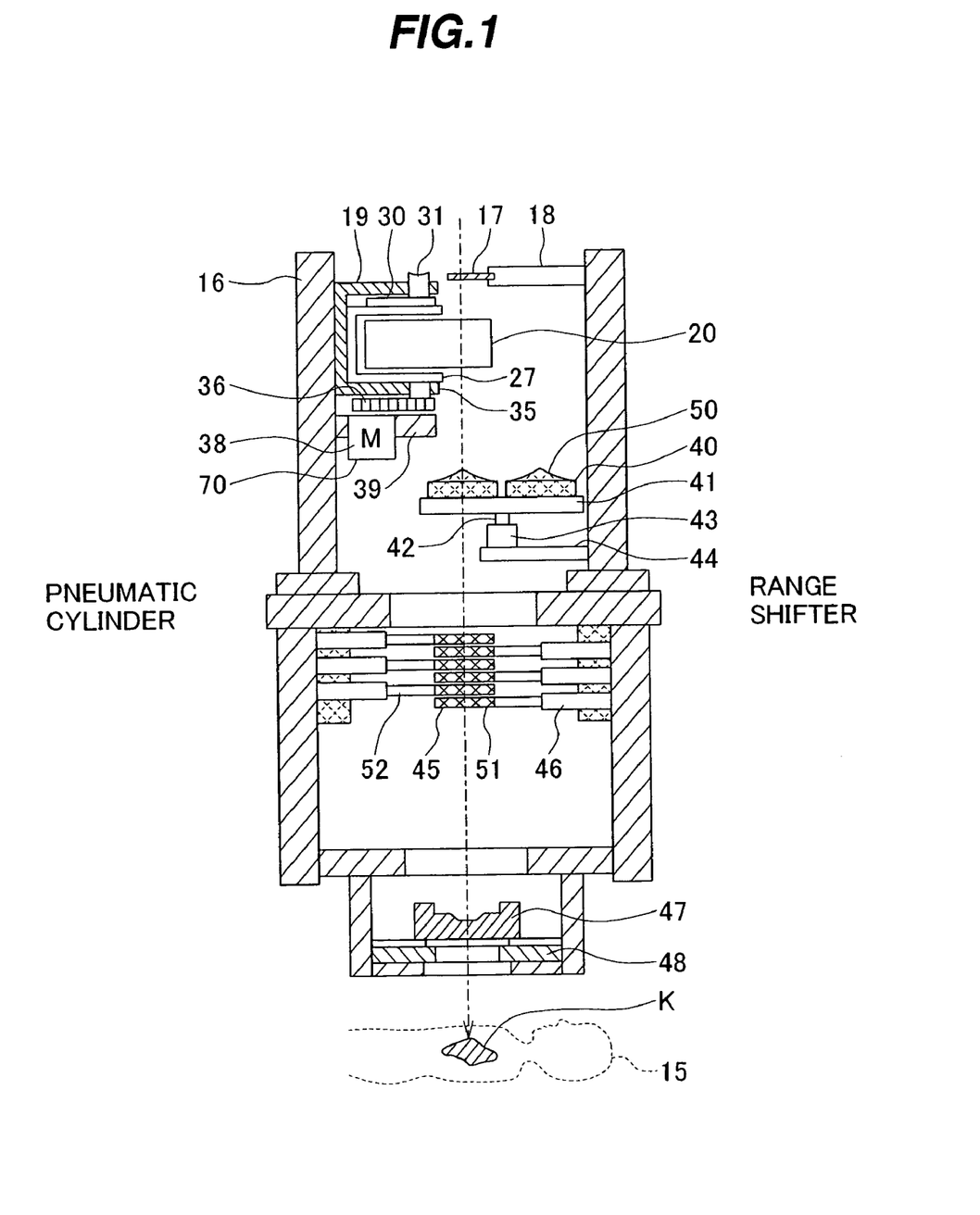
FIG. 1 is a vertical sectional view showing a detailed structure of an irradiation field forming apparatus provided in a charged particle therapy system according to a first embodiment of the present invention.

A detailed structure of the irradiation field forming apparatus 13 used in the charged particle therapy system 1 will be described below with reference to FIG. 1.

The irradiation field forming apparatus 13 has a casing 16 mounted to the inverted U-shaped section 11. On an ion beam path (beam axis) m within the casing 16, a first scatterer 17, an RMW device (range modulation wheel device) 20, a second scatterer device 40, a range adjustment device (e.g., a range shifter) 45, a bolus 47, and a collimator 48 are arranged successively in this order from the upstream side in the direction of passing of the ion beam. The first scatterer 17 is set in a support member 18 mounted to an inner surface of the casing 16. The second scatterer device 40 comprises a plurality of second scatterers 50, a rotating table 41, and a motor 43. The motor 43 is mounted on a support member 44 mounted to the inner surface of the casing 16. The rotating table 41 is mounted to a rotary shaft 42 that is coupled to a rotary shaft (not shown) of the motor 43. The plurality of second scatterers 50 are arranged on the rotating table 41 side by side in the circumferential direction thereof. The range adjustment device 45 comprises a plurality of absorbers 51 differing in thickness from each other, and an absorber operating device 46 provided for each of the absorbers 51. The absorber operating device 46 includes, though not shown, a pneumatic cylinder to which compressed air is supplied, and a piston sliding in the cylinder. Each absorber 51 is coupled to a piston rod 52 attached to the piston. The bolus 47 and the collimator 48 are also installed in the casing 16.

The first scatterer 17 has the function of scattering and spreading the ion beam passing it in the direction perpendicular to the beam axis m. The first scatterer 17 is made of a material having the large atomic number, such as lead or tungsten, which has a small energy loss with respect to a scattering rate of the ion beam. The second scatterer 50 scatters the ion beam, of which dose distribution has been spread into the Gaussian form by the first scatterer 17 in the direction perpendicular to the beam axis m, so as to have a uniform dose distribution in that perpendicular direction. The absorber 51 has the function of adjusting the range of the ion beam in the body of the patient 15 under treatment.

Figure 3:
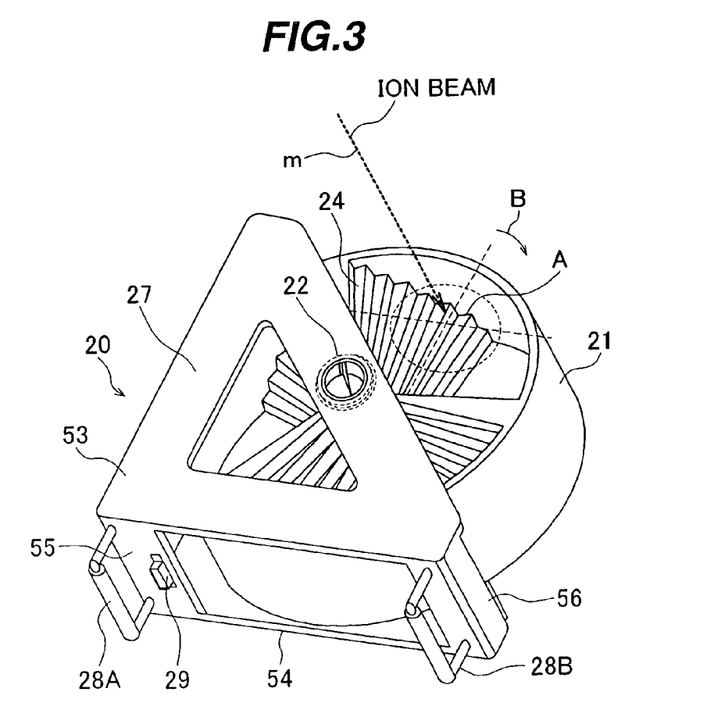
FIG. 3 is a perspective view of an RMW device in FIG. 1.
Figure 4:
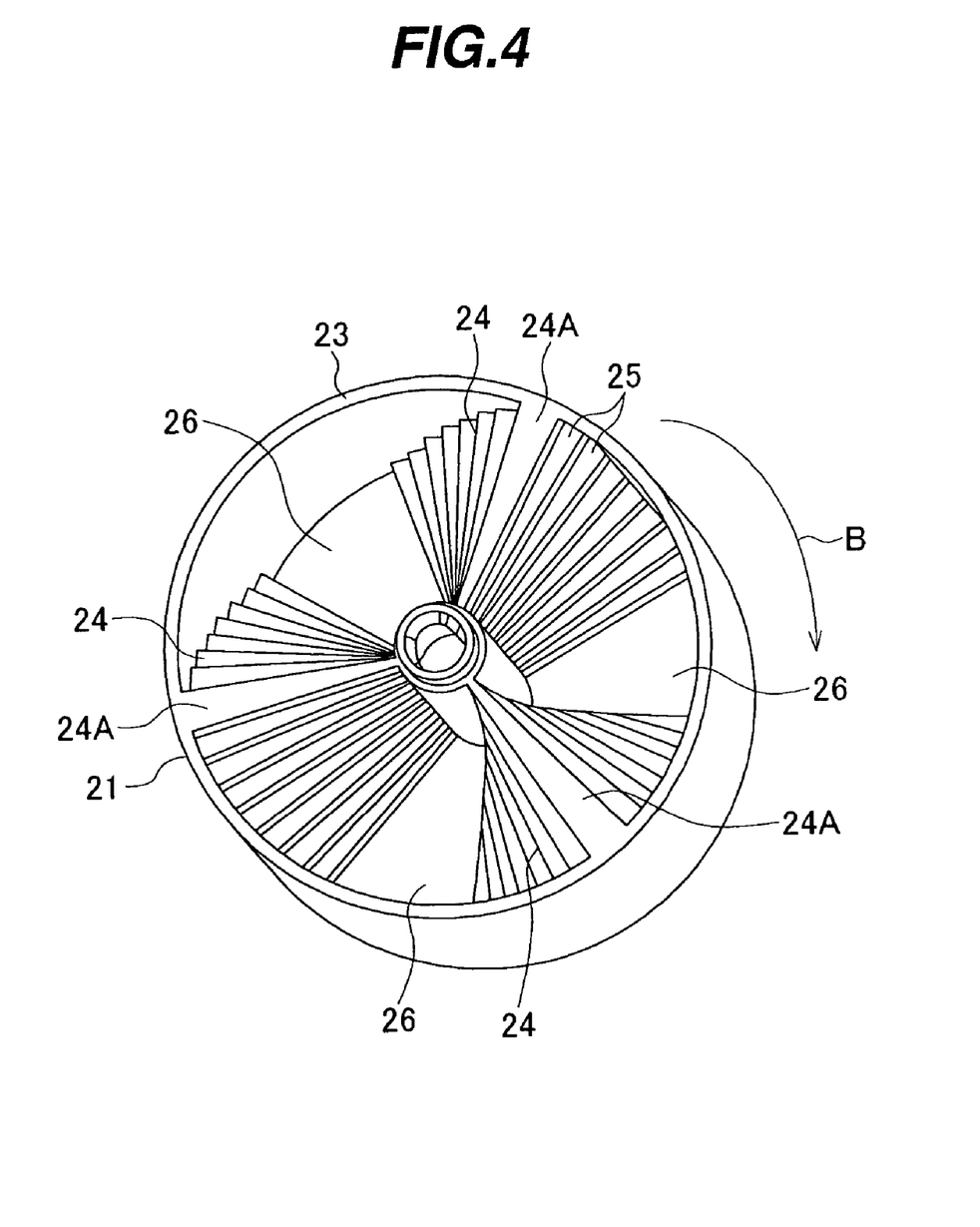
FIG. 4 is a perspective view of a RMW in FIG. 3.

A detailed structure of the RMW device 20 will be described below with reference to FIGS. 3 and 4. The RMW device 20 comprises an RMW (range modulation wheel) 21 and a housing 27. The RMW 21 has a rotary shaft 22 and a cylindrical member 23 which are disposed in a concentric relation to each other. A plurality (three in this embodiment) of blades 24 are mounted to the rotary shaft 22 and are extended in the radial direction of the RMW 21. Outer ends of the blades 24 are joined to the cylindrical member 23. Each of the blades 24 has a circumferential width larger at the outer end nearer to the cylindrical member 23 than at the inner end nearer to the rotary shaft 22. An opening 26 is formed between adjacent two of the blades 24 in the circumferential direction of the RMW 21. The opening 26 is also formed such that its circumferential width is larger at the outer end nearer to the cylindrical member 23 than at the inner end nearer to the rotary shaft 22. Each of the blades 24 has a plurality of plane areas 25 arranged in the form of steps in the circumferential direction of the RMW 21. Each of the plane areas 25 has a different thickness relative to a bottom surface of the RMW 21 in the direction of the beam axis m (namely, levels of the plane areas 25 relative to the bottom surface of the RMW 21 differ from one another). The thickness of each plane area 25 is called here the plane area thickness. More specifically, the plane area thickness of the blade 24 is increased in a stepwise way from each of the plane areas 25 adjacent to the openings 26, which are positioned on both sides of the relevant blade 24 in the circumferential direction, toward the plane area 25 positioned at a blade top portion 24A having the largest thickness in the direction of the beam axis m. The plane areas 25 correspond to, for example, respective footboard planes of steps. Each plane area 25 is extended from the rotary shaft 22 toward the cylindrical member 23. Further, a width of each plane area 25 in the circumferential direction of the RMW 21 gradually increases from its inner end nearer to the rotary shaft 22 toward its outer end nearer to the cylindrical member 23. In one RMW 21, there are three openings 26 positioned between adjacent two of the three blades 24.

The RMW 21 is disposed within the housing 27, and the rotary shaft 22 is rotatably mounted to the housing 27. The housing 27 comprises two housing members 53, 54 positioned on both sides of the RMW 21 and each having an equilateral triangular shape, and three joint members for coupling those two housing members 53, 54 to each other at their three corners. One 55 of the three joint members couples the housing members 53, 54 to each other at their right-angled corners. Another one joint member 56 couples the housing members 53, 54 to each other at their corners each located at one end of a long side of the equilateral triangle opposite to the right angle thereof. Still another joint member (not appeared in FIG. 3) couples the housing members 53, 54 to each other at their corners each located at the other end of the long side of the equilateral triangle. The rotary shaft 22 is rotatably mounted to the housing members 53, 54. Looking at the RMW 21 from the side of the housing member 53, an almost half of the RMW 21 projects out of the housing 27. The ion beam passes through the RMW 21 in that projected-out portion. The housing members 53, 54 are disposed in positions out of interference with the ion beam path. A handle 28A and an identifier (e.g., a barcode) 29 for identifying the RMW 21 are attached to the joint member 55. A handle 28B is attached to the joint member 56.

An RMW holding member 19 (FIG. 1) for holding the RMW device 20 is mounted to the inner surface of the casing 16. The RMW holding member 19 has supports 19A, 19B (FIG. 5) opposing to each other in the direction of the beam axis m. The supports 19A, 19B are disposed in positions out of interference with the ion beam path. The RMW device 20 is inserted and held between the supports 19A and 19B. A motor 38 rotating the RMW 21 is mounted to a holding member 39 fixed to the inner surface of the casing 16. A rotary shaft 35 is rotatably mounted to the support 19B and the holding member 39. A timing belt 36 is entrained over a rotary shaft 37 (FIG. 5) coupled to the motor 38 and the rotary shaft 35 so that torque of the motor 38 is transmitted to the rotary shaft 35. The motor 38, the rotary shaft 37, the rotary shaft 35, and the timing belt 36 constitute an RMW driver (range modulation wheel driver) 70.

The structure around the RMW holding member 19 will be described in more detail with reference to FIG. 5. A retaining leaf spring 34 is disposed on a surface of the support 19B opposing to the support 19A. On end of the rotary shaft 35 is projected upward of the support 19B. A pushing member 30 is disposed on the support 19A side, and a retaining leaf spring 33 is disposed on a surface of the pushing member 30 opposing to the support 19B. An auxiliary rotary shaft 31 axially aligned with the rotary shaft 35 is rotatably mounted to the pushing member 30 and penetrates the support 19A. Two movable shafts 32A, 32B extending in the direction of the beam axis m penetrate the support 19A and are mounted to the pushing member 30. The movable shafts 32A, 32B are moved in the direction of the beam axis m by a movable shaft operating device (not shown) that comprises a cylinder to which compressed air for driving is supplied, and a piston disposed in the cylinder. The movable shafts 32A, 32B are coupled to that piston. The movable shaft operating device is installed in the casing 16. The movable shaft operating device, the movable shafts 32A, 32B, and the pushing member 30 constitute an RMW pushing device (pushing device) 71.

Figure 6:
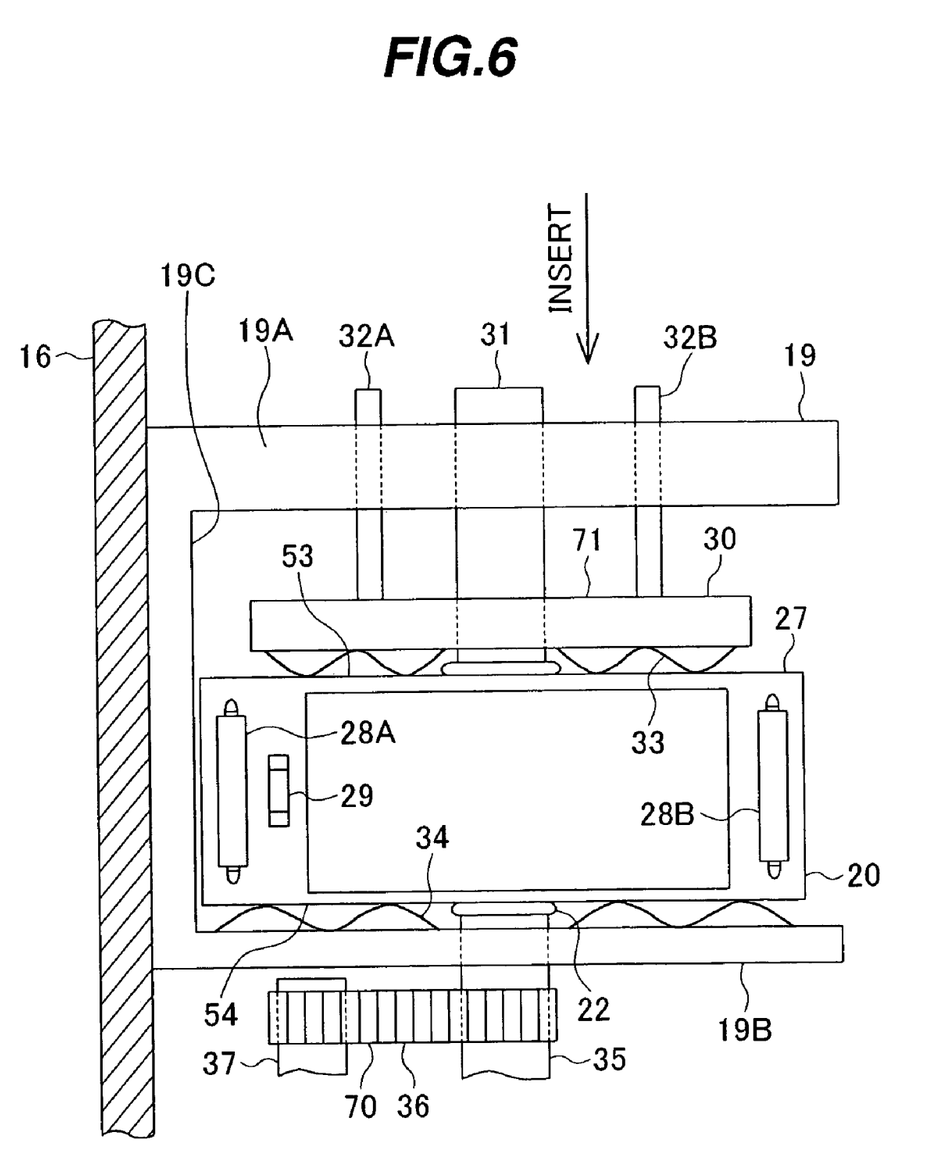
FIG. 6 is an explanatory view showing a detailed structure around the RMW holding member in FIG. 1 in the state in which the RMW device is attached in the RMW holding member.
Figure 7:
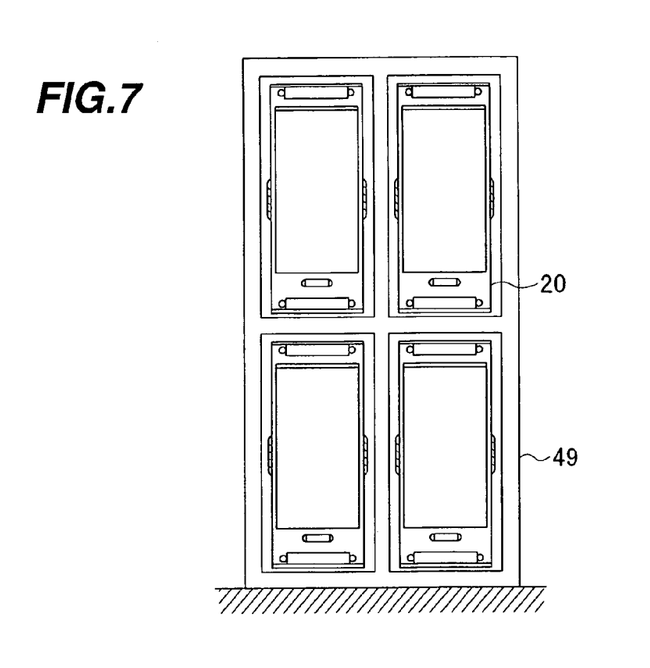
FIG. 7 is an explanatory view showing the state in which RMW devices are stored on a storage rack.

A method of installing the RMW device 20 in the casing 16 of the irradiation field forming apparatus 13 will be described below with reference to FIGS. 5 and 6. Because the RMW device 20 has the housing 27, various RMW devices can be put in a storage rack 49 in order for storage, as shown in FIG. 7. Therefore, a larger number of RMW devices 20 can be stored in the storage rack 49. The RMW device 20 matching with the ion beam irradiation conditions for a patient who is going to take treatment is taken out of the storage rack 49 and is inserted into the casing 16 through an opening (not shown) which is formed in a side wall of the casing 16 and can be opened and closed by a door (not shown). At this time, the pushing member 30 inside the RMW holding member 19 is ascended with the movable shafts 32A, 32B such that, as shown in FIG. 5, the pushing member 30 is located in a position close to the support 19A. The RMW device 20 is inserted between the pushing member 30 and the support 19B. This operation of inserting the RMW device 20 is performed by a radiation engineer (or an operator) gripping the handles 28A, 28B. The inserted RMW device 20 is detachably fixed to the RMW holding member 19 as shown in FIG. 6. In this state, the axis of the rotary shaft 22 is aligned with the axis of the rotary shaft 35, and the fore end of the rotary shaft 35 contacts the rotary shaft 22.

Then, compressed air is supplied to the cylinder of the movable shaft operating device to move the movable shafts 32A, 32B downward. Correspondingly, the pushing member 30 is descended to bring the retaining leaf spring 33 into contact with the housing member 53 of the housing 27. When the movable shafts 32A, 32B are further moved downward, the retaining leaf springs 33, 34 are compressed, whereby the housing 27 is held stationary between the pushing member 30 and the support 19B, specifically between the retaining leaf spring 33 and the retaining leaf spring 34. In this state, the rotary shaft 22 is sandwiched between the rotary shaft 35 and the auxiliary rotary shaft 31 such that respective fore ends of the rotary shaft 35 and the auxiliary rotary shaft 31 are fitted to opposite ends of the rotary shaft 22. The rotary shaft 22, the rotary shaft 35, and the auxiliary rotary shaft 31 are axially aligned with each other. At the time reaching the state in which respective fore ends of the rotary shaft 35 and the auxiliary rotary shaft 31 are fitted to the opposite ends of the rotary shaft 22, the downward movement of the movable shafts 32A, 32B is stopped. However, the auxiliary rotary shaft 31 continues to receive a pushing force against the rotary shaft 22 by the compressed air supplied from the movable shaft operating device. In this state, the rotary shaft 22 is supported by the rotary shaft 35 and the auxiliary rotary shaft 31. With the operations described above, the RMW device 20 is installed in the casing 16. After the RMW device 20 has been installed in the casing 16, the radiation engineer confirms that the rotary shaft 22 is positively fitted to the rotary shaft 35 and the auxiliary rotary shaft 31, and then closes the above-mentioned opening/closing door. The opening/closing door may be closed at the stage where the RMW device 20 has been inserted into the RMW holding member 19. The operation of opening and closing the door is remotely performed by the radiation engineer.

Getting out of sequence in description, for the patient 15 who is going to take treatment using the charged particle therapy system 1, tomographic image information including the tumor K is obtained beforehand with X-ray CT. A treatment plan is prepared based on the tomographic image information. Thus, the position of the tumor K, the irradiation field size, the incident direction, the incident energy and range of the ion beam, the Bragg peak width (SOBP width), etc. are specified for the patient 15. By using that information (hereinafter referred to as "treatment plan information") obtained from the treatment plan, the various components of the irradiation field forming apparatus 13 are set. More specifically, the RMW device 20 is installed in the casing 16 by the radiation engineer taking the RMW device 20 corresponding to the relevant patient 15 out of the storage rack 49 based on the treatment plan information. At that time, the RMW device 20 is selected based on the incident energy and the SOBP width in the treatment plan information. The SOBP width will be described in detail below. The first scatterer 17 is selected and set based on the irradiation field size and the incident energy in the treatment plan information. The first scatterer 17 may be mounted in plural on a rotating table, similarly to the second scatterers 50, such that the desired first scatterer is positioned on the beam axis m with rotation of the rotating table. Also, one of the second scatterers 50 is selected based on the irradiation field size and the incident energy in the treatment plan information, and is positioned on the beam axis m with the rotating table 41 rotated by the motor 43. Further, one of the absorbers 51 is selected based on the range in the treatment plan information, and is moved onto the beam axis m by the corresponding absorber operating device 46 such that it is properly positioned on the beam axis m. The bolus 47 and the collimator 48 are selected corresponding to the relevant patient 15 and are installed in the casing 16.

As described above, the ion beam extracted from the synchrotron 4 is irradiated to the tumor K in the body of the patient 15 after passing the first scatterer 17, the RMW device 20, the second scatterer 50, the absorber 51, the bolus 47, and the collimator 48, which are all positioned on the beam axis m.

During a period in which the ion beam is irradiated, the RMW 21 of the RMW device 20 continues rotation. The rotation of the RMW 21 is performed as follows. The torque of the motor 38 is transmitted to the rotary shaft 35 through the timing belt 36. The rotary shaft 22 fitted to the rotary shaft 35 is rotated in the direction of arrow B (FIG. 3) together with the rotary shaft 35. The auxiliary rotary shaft 31 in contact with or fitted to the rotary shaft 22 is also rotated together. At this time, while the RMW 21 is rotated in the direction of arrow B, the ion beam always passes a point A (FIG. 3) that is positioned inside the RMW device 20, but outside the housing 27, and is aligned with the beam axis m. At the position of the beam axis m, one of the openings 26 of the RMW 21, the multi-step plane areas 25 of one blade 24 arranged from that opening 26 toward the top portion 24A of the one blade 24, the multi-step plane areas 25 of the one blade 24 arranged from the top portion 24A of the one blade 24 toward the next opening 26, and the next opening 26 pass successively there. The plane areas 25 of the other two blades 24 also likewise pass the position of the beam axis m. In other words, the ion beam passes one blade 24 between the openings 26 such that it first passes successively the plurality of plane areas differing in thickness from each other (of which thickness increases gradually toward the blade top portion 24A) in order from the thinnest plane area (i.e., the plane area 25 present at the lowest position from the bottom surface of the RMW 21) toward the thickest plane area (i.e., the blade top portion 24A), and then passes successively the plurality of plane areas differing in thickness from each other (of which thickness decreases gradually toward the next opening 26) in order from the blade top portion 24A toward the next opening 26. The ion beam also passes the other two blades 24 in a similar way.

Figure 8:
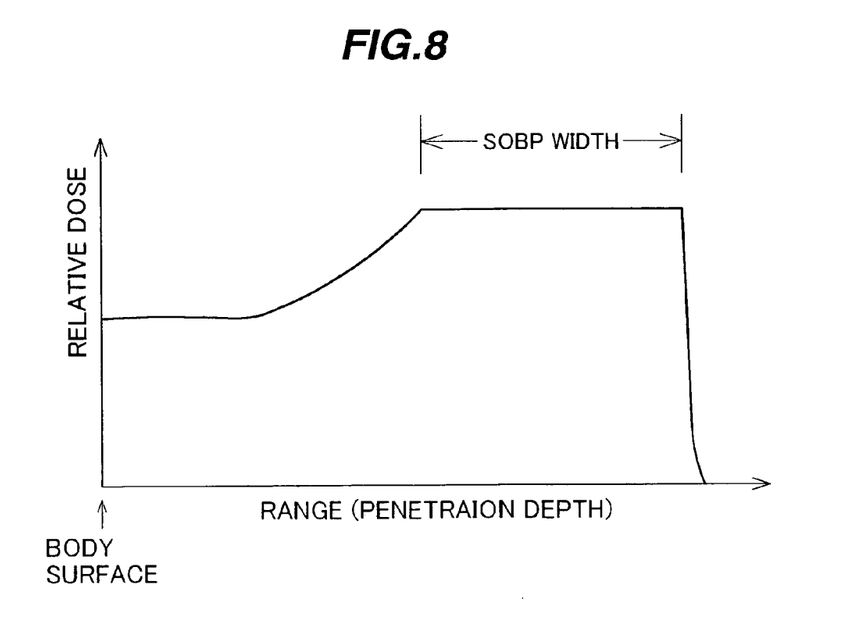
FIG. 8 is a graph for explaining an SOBP width obtained by the RMW device.

Thus, the ion beam passes a number of plane areas differing in thickness from each other, and therefore the ion beam having passed the RMW device 20 has plural levels of energy. The ion beams having different levels of energy penetrate the tumor K to different positions. The ion beam having a higher level of energy reaches a deeper position in the tumor K. Accordingly, as shown FIG. 8, a dose distribution is made uniform in the depth direction of the tumor K. A region of the dose distribution thus made uniform is called the SOBP width.

In this embodiment, the identifier 29 attached to the housing 27 is monitored to prevent the RMW device 20 from being erroneously installed. This monitoring is performed by using a barcode reader (not shown) mounted to the above-mentioned opening/closing door which is provided in the casing 16 and is opened at the time of inserting the RMW device 20 into the casing 16. More specifically, when the opening/closing door is closed, the barcode reader reads a barcode contained in the identifier 29. The barcode information read by the barcode reader is sent to a computer (not shown). Based on the barcode information and the treatment plan information, the computer (erroneous installation determining unit) determines whether the installed RMW device 20 is a predetermined one corresponding to the patient 15 who is going to take treatment, and then indicates information of a determined result on a display (not shown). If the display indicates that the installed RMW device 20 is an "erroneously installed one", the radiation engineer opens the opening/closing door, takes the erroneously installed RMW device 20 out of the casing 16, and installs the proper RMW device 20 in the casing 16. In the state in which the proper RMW device 20 is installed, the operation of the charged particle therapy system 1 is started. Thus, in that state, the ion beam extracted from the charged particle beam generator 2 is irradiated through the irradiation field forming apparatus 13 to the tumor K in the body of the patient 15 lying on the treatment couth 14.

With the above-described method of monitoring the erroneous installation of the RMW device 20, the erroneous installation can be confirmed only after the opening/closing door has been closed. As an alternative, the arrangement may be modified such that the barcode reader is mounted to another side wall of the casing 16 perpendicular to the side wall thereof in which the opening/closing door is provided, and a barcode is attached to a surface of the identifier 29 facing that another side wall. In this case, the barcode of the identifier 29 can be read by the barcode reader before pushing the RMW device 20 by the pushing member 30, when the RMW device 20 is inserted into the RMW holding member 19. Therefore, the erroneous installation of the RMW device 20 can be confirmed before closing the opening/closing door. It is hence possible to eliminate the operations of pushing and releasing the pushing member 30, and closing and opening the opening/closing door, which are required to take out the erroneously installed RMW device 20 after installation thereof in the above-described case where the barcode reader is mounted to the opening/closing door.

The erroneous installation of the RMW device 20 can also be confirmed by the radiation engineer looking at the identifier containing identification information that is discernable by the radiation engineer. Instead of using the barcode, the identifier may be designed to make electric shortening at its rear side so as to electrically detect the specific number of the identifier by utilizing a bit pattern. Further, the identifier may be constituted by a plurality of limit switches, and limit switch docks for pushing the limit switches may be provided on the casing.

According to this embodiment, since the RMW 21 is mounted to the housing 27, positioning of the RMW device 20 to the center of rotation (where the rotary shaft 22 is to be positioned) can be easily performed by placing the housing 27 in contact with the casing 16 or the holding member (e.g., the RMW holding member 19) provided in the casing 16. Hence, the axis of the rotary shaft 22 of the RMW 21 can be simply aligned with the axis of the rotary shaft 35 on the driving side in a short time. In other words, the RMW 21 can be installed in alignment with the rotary shaft on the driving side in a short time. This contributes to cutting a time required for setting the various components of the irradiation field forming apparatus 13 (such as the first scatterer 17, the RMW 21, and the second scatterer 50) corresponding to the patient 15, and to cutting a treatment time per patient. The treatment time means a time practically taken for treatment from the setting of those components to the end of irradiation of the ion beam to the patient 15. Cutting of the treatment time in the charged particle therapy system 1 having the RMW device 20 leads to an increased number of patients treated.

Since the RMW device 20 has the housing 27, it can be placed in the storage rack 49 by directly putting the housing 27 on a rack shelf. Therefore, the RMW device 20 can be stored in order without tilting (see FIG. 7), and a larger number of RMW devices 20 can be stored in a certain storage space. Conversely, when the number of RMW devices 20 to be stored is decided, a required storage space can be reduced. Also, since the RMW 21 is mounted in and protected by the housing 27, a risk of damage of the RMW 21, in particular the blades 24, can be reduced in handling of the RMW 21 not only when the RMW 21 is inserted into the casing 16 (including carrying of the RMW 21 from the storage rack 49), but also when the RMW 21 is removed from the casing (including carrying of the RMW 21 back to the storage rack 49). Further, according to this embodiment, by operating the RMW pushing device 71, the RMW device 20 can be easily fixed in the casing 16, and the rotary shaft 35 of the RMW driver 70 can be fitted to the rotary shaft 22 of the RMW 21. Removal of the RMW device 20 from the casing 16 can also be easily performed by operating the RMW pushing device 71 in the reversed direction. When inserting the RMW device 20 into the casing 16 or when removing the RMW device 20 from the casing 16, the radiation engineer grasps the handles 28A, 28B of the RMW device 20 without directly touching the RMW 21. This results in reduced dose that the radiation engineer handing the RMW device 20 receives. In addition, since the RMW device 20 has the identifier 29 attached to the housing 27 being not rotatable, it is possible to readily read the identification information of the RMW device 20 and to easily confirm erroneous insertion (or erroneous installation) of the RMW device 20.

[Second Embodiment]

Figure 9A:
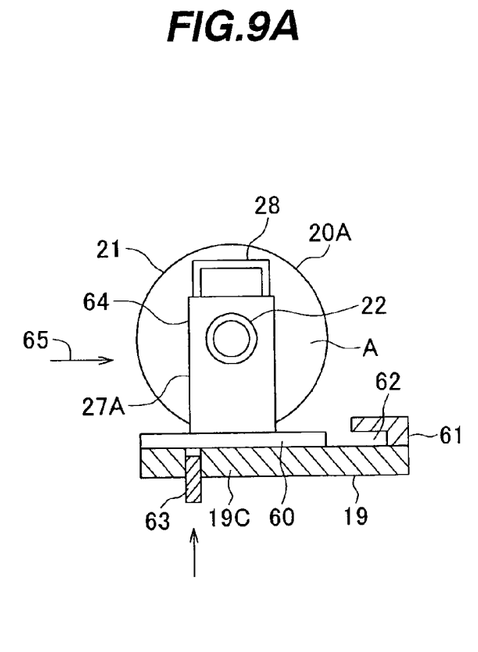
FIG. 9A is an explanatory view showing the state before the RMW device is attached in the RMW holding member.
Figure 9B:
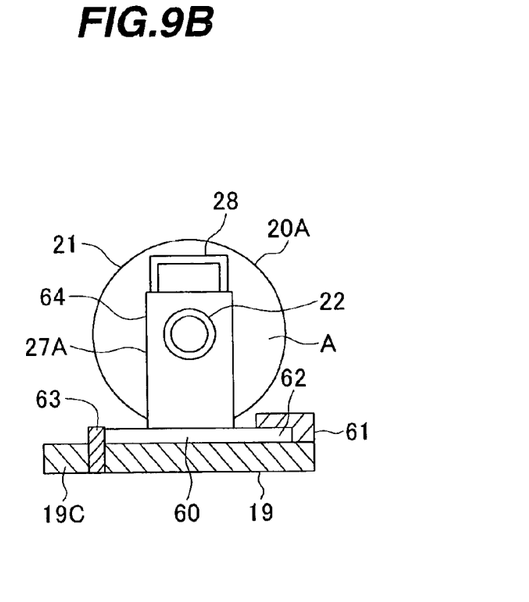
FIG. 9B is an explanatory view showing the state after the RMW device has been attached in the RMW holding member.

A charged particle therapy system according to a second embodiment of the present invention will be described below. The charged particle therapy system of this second embodiment differs only in the structure of the RMW device from the charged particle therapy system 1 of the above-described first embodiment. In other words, the charged particle therapy system of this embodiment has the same structure as that of the charged particle therapy system 1 except for the RMW device. As shown in FIG. 9, an RMW device 20A used in this embodiment has a joint member 60 in the form of a flat plate, which corresponds to the joint member 55, etc. of the RMW device 20. The joint member 60 couples a pair of housing members 64 to each other. The pair of housing members 64 are arranged in an opposed relation with the RMW 21 disposed between them. The rotary shaft 22 of the RMW 21 is rotatably mounted at its opposite ends to the pair of housing members 64. A handle 28 is attached to each of the housing members 64. The pair of housing members 64 are mounted to the joint member 60 so as to extend from it perpendicularly. A housing 27A is made up of the joint member 60 and the pair of housing members 64.

Figure 5:
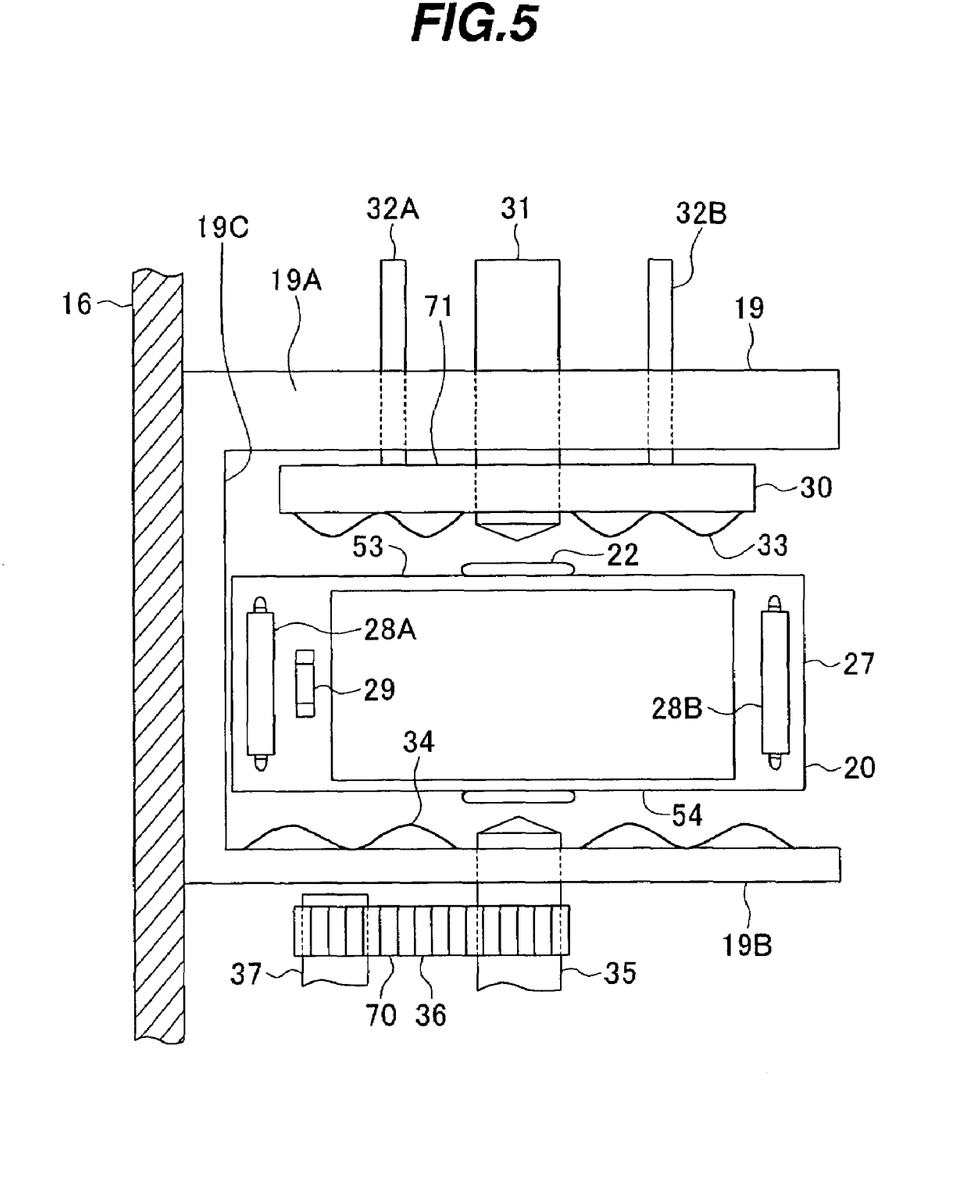
FIG. 5 is an explanatory view showing a detailed structure around an RMW holding member in FIG. 1 in the state in which the RMW device is inserted in the RMW holding member.

The RMW device 20A is inserted into a space between the support 19A and the support 19B of the RMW holding member 19 in the direction from the right to the left as viewed in FIG. 5. At this time, the pushing member 30 is located in the position shown in FIG. 5. In this second embodiment, unlike the first embodiment, the opening/closing door is provided in a side wall of the casing 16 positioned on the right side as viewed in FIG. 5. In this embodiment, the RMW device 20A is inserted into the casing 16 after opening the opening/-closing door thus provided. When the joint member 60 of the RMW device 20A inserted between the support 19A and the support 19B strikes against a vertical portion 19C (see FIGS. 5 and 9) of the RMW holding member 19 which is extended in the vertical direction, the operation of pushing the RMW device 20A is stopped. Then, the RMW device 20A is moved horizontally in the direction of arrow 65 in FIG. 9A such that one end of the joint member 60 is inserted into an RMW insertion groove 62. The RMW insertion groove 62 is formed between the vertical portion 19C and a retaining member 61 mounted to the vertical portion 19C. The retaining member 61 and the RMW insertion groove 62 are extended in the vertical direction. When one end of the joint member 60 inserted into the RMW insertion groove 62 strikes against the retaining member 61, a stopper 63 disposed in the side wall of the casing 16 (not shown in FIGS. 9A and 9B) and the vertical portion 19C is pushed to project out. The stopper 63 contacts a face of the other end of the joint member 60 to prevent the joint member 60 from slipping off from the RMW insertion groove 62. In this way, the RMW device 20A is held by the RMW holding member 19. Thereafter, as in the first embodiment, the pushing member 30 is descended to fixedly hold the RMW device 20A in place. This second embodiment can also provide similar advantages to those obtained with the first embodiment.

What is claimed is:

1. A charged particle therapy system including a charged particle beam generator for generating a charged particle beam and a charged particle beam irradiation apparatus comprising a range modulation wheel device through which the charged particle beam emitted from said charged particle beam generator passes, wherein said range modulation wheel device comprises a housing and a range modulation wheel disposed in said housing and rotatably mounted thereto so as to allow the charged particle beam to pass through the range modulation wheel.

2. A charged particle therapy system according to claim 1, wherein said charged particle beam irradiation apparatus further comprises a holding member for holding said range modulation wheel device in such a manner that the range modulation wheel device can be inserted into and removed from said holding member.

3. A charged particle therapy system according to claim 1 or 2, wherein said charged particle beam irradiation apparatus further comprises a range modulation wheel driver having a second rotary shaft in contact with a first rotary shaft of said range modulation wheel.

4. A charged particle therapy system according to claim 2, wherein said charged particle beam irradiation apparatus further comprises a pushing device for pushing said range modulation wheel device against said holding member in a releasable way.

5. A charged particle therapy system according to claim 1, wherein an identifier is attached to said housing and given with identification information for identifying said range modulation wheel device, and said charged particle therapy system further includes an erroneous installation determining unit for receiving the identification information and determining erroneous installation of said range modulation wheel device.

6. A charged particle therapy system according to claim 2, wherein an identifier is attached to said housing and given with identification information for identifying said range modulation wheel device, and said charged particle therapy system further includes an erroneous installation determining unit for receiving the identification information and determining erroneous installation of said range modulation wheel device.

7. A charged particle therapy system according to claim 3, wherein an identifier is attached to said housing and given with identification information for identifying said range modulation wheel device, and said charged particle therapy system further includes an erroneous installation determining unit for receiving the identification information and determining erroneous installation of said range modulation wheel device.

8. A charged particle therapy system according to claim 4, wherein an identifier is attached to said housing and given with identification information for identifying said range modulation wheel device, and said charged particle therapy system further includes an erroneous installation determining unit for receiving the identification information and determining erroneous installation of said range modulation wheel device.

9. A charged particle therapy system according to claim 1, wherein said range modulation wheel has a blade having a thickness different stepwise in the direction of passing of the charged particle beam.

10. A charged particle beam generator according to claim 9, wherein said range modulation wheel has a plurality of blades and an opening between two blades adjacent in the circumferential direction.

11. A range modulation wheel device comprising a housing and a range modulation wheel disposed in said housing and rotatably mounted thereto so as to allow a charged particle beam to pass through said range modulation wheel, said range modulation wheel having at least one blade having a thickness different stepwise in the direction of passing of the charged particle beam.

12. A range modulation wheel device according to claim 11, wherein said housing includes an identifier attached thereto.

13. A method of installing a range modulation wheel device, the method comprising the steps of:

preparing a range modulation wheel device comprising a housing and a range modulation wheel disposed in said housing and rotatably mounted thereto;

inserting said range modulation wheel device into a holding member provided in a charged particle beam irradiation apparatus; and pushing said housing against said holding member by a pushing member.

14. A method of installing a range modulation wheel device according to claim 13, further comprising the step of determining erroneous installation of said range modulation wheel device based on identification information attached to said housing by using an erroneous installation determining unit.

* * * * *